US006027892A

United States Patent [19]
Chang et al.

[11] Patent Number: 6,027,892
[45] Date of Patent: Feb. 22, 2000

[54] COMPOSITIONS AND METHODS FOR REDUCING RADIATION AND DRUG RESISTANCE IN CELLS

[76] Inventors: Esther H. Chang, 7508 Vale St., Chevy Chase, Md. 20815; Kathleen F. Pirollo, 2001 N. Adams St. #1031, Arlington, Va. 22201

[21] Appl. No.: 08/991,830

[22] Filed: Dec. 16, 1997

Related U.S. Application Data

[60] Provisional application No. 60/034,160, Dec. 30, 1996.

[51] Int. Cl.[7] .............................. C12Q 1/68; C12N 9/00; C12N 15/85; C07H 21/04
[52] U.S. Cl. .............................. 435/6; 435/194; 435/371; 435/375; 536/23.1; 536/24.31; 536/24.5
[58] Field of Search .............................. 435/6, 91.1, 183, 435/172.3, 194, 320.1, 371, 375, 440, 455; 536/23.1, 24.31, 24.5; 514/44

[56] References Cited

U.S. PATENT DOCUMENTS

| | | | |
|---|---|---|---|
| 5,576,208 | 11/1996 | Monia et al. | 435/240.2 |
| 5,599,704 | 2/1997 | Thompson et al. | 435/325 |
| 5,734,039 | 3/1998 | Calabretta et al. | 536/24.5 |

FOREIGN PATENT DOCUMENTS

WO 95/32987   12/1995   WIPO .

OTHER PUBLICATIONS

Denner, Ia et al. (Jul. 21, 1994) WO9415645–A. Database: Geneseq, Q67036 (Accessed Jul. 24, 1998).
Kasid et al. Science, Mar. 10, 1989. vol. 243, pp. 1354–1356.
Daum et al. TIBS 19, 474–480 (Nov. 1994).
Tseng et al. Cancer Gene Therapy. vol 1 (1), pp. 65–71 (Mar. 1994).
Branch, A.D. TIBS 23, 45–50 (Feb. 1998).
Gewirtz et al. PNAS. 93, 3161–3163 (Apr. 1996).
Rojanasakul. Advanced Drug Delivery Review. 18, 115–131 (Jan, 30, 1996).
Maher et al. Archives of Biochemistry and Biophysics. Vol. 253, pp. 214–220 (Feb. 15, 1987).
Gura, T. Science, vol. 278, pp. 1041–1042 (Nov. 1997).
Crooke, S.T. Chapter 1, Basic Principles of Antisense Therapeutics on "Antisense Research And Application" (ed. Stanley T. Crooke), Springer–Verlag, New York, (Jul. 1998) pp. 1–50.
Betram, J., et al., "Reduction of erbB2 gene product in mamma carcinoma cell lines by erbB2 mRNA–specific and tyrosine kinase consensus phosphorothioate antisense oligonucleotides", (1994) Biochem. Biophys. Res. Commun. 200:661–667.
Bradley, Matthews O., et al., "Reversal of Transformed Phenotypes by Antisense fos", (1992) Annals New York Academy of Sciences, pp. 124–135.
Daum, Günter, et al., "The ins and outs of Raf kinases", (1994) Trends Biochem. Sci. 19, 474–480.
Dean, N.M., et al., "Antisense oligonucleotides as inhibitors of signal transduction: development from research tools to therapeutic agents", (1996) Biochem. Soc. Trans. 24, 623–629.
Kasid, U., et al., "Effect of Antisense c–raf–1 on Tumorigenicity and Radiation Sensitivity of a Human Squamous Carcinoma", (1989) Science 243, 1354–1356.
Kasid, U., et al., "The raf Oncogene is Associated with a Radiation–Resistant Human Laryngeal Cancer", (1987) Science 237, 1039–1041.
Kizaka–Kondoh, Shinae, et al., "Raf–1 Protein Kinase Is an Integral Component of the Oncogenic Signal Cascade Shared by Epidermal Growth Factor and Platelet–Derived Growth Factor", (1992) Mol. Cell. Biol. 12:5078–5086.
Ledwith, Brian J., et al., "Antisense–fos RNA Causes Partial Reversion of the Transformed Phenotypes Induced by the c–Ha–ras Oncogene", (1990) Mol. Cell. Biol. 10:1545–1555.
Sepp–Lorenzino, Laura, et al., "Signal transduction pathways induced by heregulin in MDA–MB–453 breast cancer cells", (1996) Oncogene, 12, 1679–1687.
Soldatenkov, MD, V.A., et al., "Inhibition of Raf–1 Protein Kinase by Antisense Phosphorothioate Oligodeoxyribonucleotide Is Associated with Sensitization of Human Laryngeal Squamous Carcinoma Cells to Gamma Radiation", (1997) The Cancer Journal from Scientific American 3, 13–20.
Suy, Simeng, et al., "Association of Grb2 with Sos and Ras with Raf–1 upon gamma irradiation of breast cancer cells", (1997) Oncogene, 15, 53–61.
Vaughn, James P., et al., "Inhibition of the erbB–2 tyrosine kinase receptor in breast cancer cells by phosphoromonothioate and phosphorodithioate antisense oligonucleotides", (1996) Nucleic Acids Res., 24, 4558–4564.

*Primary Examiner*—John S. Brusca
*Assistant Examiner*—Mark L. Shibuya
*Attorney, Agent, or Firm*—Rothwell, Figg, Ernst & Kurz, P.C.

[57] ABSTRACT

Provided are antisense oligonucleotides directed against the raf-1 gene, Ha-ras gene and HER-2 gene, components of a signal transduction pathway involving oncogenes and their normal counterparts and leading to the phenotype of cellular radioresistance. Administration of these antisense oligonucleotides is shown to reverse the radioresistance phenotype in cells overexpressing HER-2 or a mutant form of Ha-ras. Methods and compositions for reversing radiation resistance among other conditions involving these genes are disclosed.

12 Claims, 7 Drawing Sheets

SEQUENCE LISTING (1) GENERAL INFORMATION:

(iii) NUMBER OF SEQUENCES:  9

(2) INFORMATION FOR SEQ ID NO:1:

(i) SEQUENCE CHARACTERISTICS:
      (A) LENGTH: 18 base pairs
      (B) TYPE: Nucleic acid
      (C) STRANDEDNESS: Single
      (D) TOPOLOGY: Linear (ii) MOLECULE TYPE: DNA (xi) SEQUENCE DESCRIPTION: SEQ ID NO:1:

TCCCTGTATG TGCTCCAT                                                   18

(2) INFORMATION FOR SEQ ID NO:2:

(i) SEQUENCE CHARACTERISTICS:
      (A) LENGTH: 11 base pairs
      (B) TYPE: Nucleic acid
      (C) STRANDEDNESS: Single
      (D) TOPOLOGY: Linear (ii) MOLECULE TYPE: DNA (xi) SEQUENCE DESCRIPTION: SEQ ID NO:2:

TATTCCGTCA T                                                         11

(2) INFORMATION FOR SEQ ID NO:3:

(i) SEQUENCE CHARACTERISTICS:
      (A) LENGTH: 15 base pairs
      (B) TYPE: Nucleic acid
      (C) STRANDEDNESS: Single
      (D) TOPOLOGY: Linear (ii) MOLECULE TYPE: DNA (xi) SEQUENCE DESCRIPTION: SEQ ID NO:3:

TCCATGGTGC TCACT                                                15

(2) INFORMATION FOR SEQ ID NO:4:

(i) SEQUENCE CHARACTERISTICS:
      (A) LENGTH: 18 base pairs
      (B) TYPE: Nucleic acid
      (C) STRANDEDNESS: Single
      (D) TOPOLOGY: Linear (ii) MOLECULE TYPE: DNA (xi) SEQUENCE DESCRIPTION: SEQ ID NO:4:

ATGGAGCACA TACAGGGA                                               18

(2) INFORMATION FOR SEQ ID NO:5:

(i) SEQUENCE CHARACTERISTICS:
        (A) LENGTH: 18 base pairs
        (B) TYPE: Nucleic acid
        (C) STRANDEDNESS: Single
        (D) TOPOLOGY: Linear (ii) MOLECULE TYPE: DNA (xi) SEQUENCE DESCRIPTION: SEQ ID NO:5:

CTAGCCTATC TGTCTTCG                                                      18

(2) INFORMATION FOR SEQ ID NO:6:

(i) SEQUENCE CHARACTERISTICS:
        (A) LENGTH: 11 base pairs
        (B) TYPE: Nucleic acid
        (C) STRANDEDNESS: Single
        (D) TOPOLOGY: Linear (ii) MOLECULE TYPE: DNA (xi) SEQUENCE DESCRIPTION: SEQ ID NO:6:

TTATACGTCC T                                                              11

(2) INFORMATION FOR SEQ ID NO:7:

(i) SEQUENCE CHARACTERISTICS:
        (A) LENGTH: 11 base pairs
        (B) TYPE: Nucleic acid
        (C) STRANDEDNESS: Single
        (D) TOPOLOGY: Linear (ii) MOLECULE TYPE: DNA (xi) SEQUENCE DESCRIPTION: SEQ ID NO:7:

TTATACGTCC T                                                             11

(2) INFORMATION FOR SEQ ID NO:8:

(i) SEQUENCE CHARACTERISTICS:
        (A) LENGTH: 15 base pairs
        (B) TYPE: Nucleic acid
        (C) STRANDEDNESS: Single
        (D) TOPOLOGY: Linear (ii) MOLECULE TYPE: DNA (xi) SEQUENCE DESCRIPTION: SEQ ID NO:8:

CACTGGTTGC ACCTT                                                   15

(2) INFORMATION FOR SEQ ID NO:9:

(i) SEQUENCE CHARACTERISTICS:
        (A) LENGTH: 15 base pairs
        (B) TYPE: Nucleic acid
        (C) STRANDEDNESS: Single
        (D) TOPOLOGY: Linear (ii) MOLECULE TYPE: DNA (xi) SEQUENCE DESCRIPTION: SEQ ID NO:9:

CTAGCCATGC TTGTC                                                   15

COMPOSITIONS AND METHODS FOR REDUCING RADIATION AND DRUG RESISTANCE IN CELLS

This application is related to provisional application Ser. No. 60/034,160, filed Dec. 30, 1996, to which priority is claimed.

The failure of a significant number of tumors to respond to drug and/or radiation therapy is a serious problem in the treatment of cancer. While the genetic basis of this resistance in mammalian cells is still poorly understood, evidence has been obtained in recent years linking proto-oncogenes and oncogenes to the phenomenon of cellular radiation resistance.

The earliest report of such a possible link was that of FitzGerald et al. in 1985 [FitzGerald, T. J. et al. (1985) Am. J. Clin. Oncol. 8: 517–522], who found that transfection of NIH 3T3 cells with a human N-ras oncogene was able to increase the radiation resistance level of the recipient cell line. Expanding upon this was the report by Sklar [Sklar, M. D. (1988) Science 239: 645–647] that NIH 3T3 cells transformed not only by N-ras but also by mutated Ha- and Ki-ras were more radiation resistant than the parent cell line. Additionally, we demonstrated a similar effect on the radiation resistance level of NIH 3T3 cells by both the mutated form of Ha-ras and the overexpression of the Ha-ras proto-oncogene [Pirollo, K. F. et al. (1989) Int. J. Radiat. Biol. 55: 783–796]. A synergistic increase in the radiation resistance level of primary rat embryo cells was also seen after cotransfection of ras and myc oncogenes [Ling, C. C. and B. Endlich (1989) Radiat. Res. 120: 267–279; McKenna, W. G. et al. (1990) Cancer Res. 20: 97–102]. All documents cited herein supra and infra are hereby incorporated in their entirety by reference thereto.

The association was extended to include other oncogenes when transfection of NIH 3T3 cells by high molecular weight DNA from both radiation-resistant cells derived from a human laryngeal squamous carcinoma [Kasid, U. et al. (1987) Science 237: 1039–1041] and radiation-resistant noncancerous skin fibroblast (NSF) cell lines from members of a family with Li-Fraumeni syndrome [Pirollo et al., 1989, supra; Chang, E H. et al. (1987) Science 237: 1036–1039] led to the identification of an activated human raf-1 oncogene in the resulting radiation-resistant transformants. Transfections not only of the raf-1 oncogene but also of other protein-serine kinase encoding oncogenes, mos and cot, have been shown to confer the radiation-resistant phenotype on the recipient human Beas-2B [Kasid, U. et al. (1989) Abstract, 5th Annual Meeting on Oncogenes] mouse NIH 3T3 (Pirollo et al.,1985, supra) and hamster SHOK cells [Suzuki, K. et al. (1992) Radiat. Res. 129: 157–162], respectively. The effect of activated oncogenes on the radiation resistance level of NIH 3T3 cells is not a generalized phenomenon but is particular to specific oncogenes, as was clearly shown by Sklar [Sklar, 1988, supra; Sklar, M. D. et al. (1986) Int. J. Radiat. Oncol. Biol. Phys. 12: 190–191, Abstract] for abl and fms and by our laboratory [Pirollo et al., 1985, supra] for myc, fes, and abl.

Evidence continues to accumulate which indicates that the normal counterpart of many of the known oncogenes (proto-oncogenes) are involved in vital, normal cellular functions [Bishop, J. M. (1991) Cell 64: 235–248; Cantley, L. C. et al. (1991) Cell 64: 281–302; Hunter, T. (1991) Cell 64: 249–270]. They have also been shown to interact with one another as components of a proposed signal transduction pathway which involves transmission of messages from the membrane to the nucleus directing the cells to divide or to differentiate. On the basis of antibody-blocking experiments, it has been proposed that raf-1 is downstream of ras in this pathway [Morrison, D. K. (1990) Cancer Cells 2: 377–380; Rapp, U. R. et al. (1988) In The Oncogene Handbook, T. Curran, J. E. P. Reddy and A Skala, Eds, pp. 213–252. Elsevier, Amsterdam; Smith, M. R. et al. (1986) Nature 320: 540–543; Weinstein, I. B. (1988) Mutat. Res. 202: 413–420].

Part of the signal transduction pathway leading to raf-1 expression is HER-2 (c-erb B-2/neu) which encodes a transmembrane protein tyrosine kinase with extensive homology to the epidermal growth factor receptor (EGF-R). Elevation of HER-2 in cancer cells has been shown to correlate with failure to respond to radiation therapy and there is significant evidence that expression of HER-2 affects the response of breast cancer tumors to endocrine therapy with Tamoxifen, and chemotherapy using drugs such as cisplatin, carboplatin, 5-fluorouracil, mitoxantrone, cyclophosphamide, methotrexate, doxorubicin, carmustine, melphalan, mitomycin, etoposide and combinations of these drugs [Pegram, M. D. et al. (1993) Proc. 84th Ann. Mtg. of AACR, Orlando, 19–22 May 1993 34, p26 (Abstract); Wright, C. et al. (1992b) Br. J. of Can. 65: 271–274; Allred, D. C. et al. (1992) J. Clin. Onc. 10: 599–605; Gusterson, B. A. et al. (1992) J. Clin. Onc. 10: 1049–1056; Van Diest, P. J. et al. (1988) Path. Res. Pract. 188: 344–349; Muss, H. B. et al (1994) NEJM 330: 1260–1266; Tsai, C.-M. et al. (1993) J. Natl. Can Inst. 85: 897–901].

Recent studies indicate that the radiation resistant (RR) phenotype appears to be linked to the activation of specific protooncogenes in a signal transduction pathway involving HER-2 as an upstream member of the pathway and Ha-ras and raf-1 downstream of HER-2, analogous to that described for cell growth and differentiation [Pirollo, K. F. et al. (1993) Rad. Res. 135:234–243]. We hypothesized that disruption of the pathway therefore should lead to reversal of this phenotype and increased sensitivity of resistant cell to drug/radiation therapy which would have far reaching clinical implications in the treatment of drug and radiation resistant tumors.

SUMMARY OF THE INVENTION

A specific strategy to interfere with the signaling is to modulate the expression of specific genes in the pathway at the RNA level using antisense oligonucleotides (ASO). Short antisense DNA oligonucleotides selectively bind to cellular mRNA targets through complementary sequence-specific Watson-Crick base pairing. The hydrogen-bonded antisense molecule can modulate the expression of the targeted gene product [Uhlmann, E. and Pyman, A. (1990) Chem. Rev. 90: 544–584]. We and others have demonstrated the ability of antisense oligonucleotides and their modified analogues to specifically inhibit ras p21 protein synthesis in in vitro translation, in cell culture, and in tumorigenesis in nude mice [Yu, Z. et al. (1989) J. Experim. Path. 4: 97–108; Brown, D. et al. (1989) Oncogene Res. 4: 243–252; Chang, E. H. et al. (1991) Biochemistry 30: 8283–8286; Ts'o, P. O. P. et al. (1992) Annals. N. Y. Aca. Sci. 660:150–177; Plenat, F. (1997) Mol. Med. Today 6: 225–267]. Additionally, ASO against genes such as c-myb, c-myc, c-fos, BCR-ABL and the IGF receptor, have also been shown to suppress human tumor cell growth in vitro and in some cases are currently in clinical trials as anti-cancer therapeutics [Stein, C.A. et al. (1988) Nucl. Acids. Res. 16: 3209–3221; Mercola, D. and Cohen, J. S. (1995) Cancer Gene Ther.2:47–59; Scanlon, K. J. et al. (1995) FASEB J. 9: 1288–1296].

The serine/threonine kinase Raf-1 protein appears to be a central component of multiple signal transduction pathways in the cell [Reviewed in: Campbell, J. S. et al. (1995) *Rec. Prog. Hormone. Res.* 50: 131–159; Daum, G. et al. (1994) *TIBS* 19: 474–480] including that for radiation resistance. Consequently, the use of ASO against raf-1 itself, or against upstream effectors of raf-1 such as Ha-ras and HER-2, to impede signaling through this gene should result in increased drug and radiation sensitivity, which would have far reaching clinical implications in the treatment of radioresistant tumors.

Therefore, the present invention relates to a method for reversing the drug and radiation resistance phenotype of cells, more specifically tumor cells which have acquired drug and/or radiation resistance. The method of the present invention employs antisense oligonucleotides targeted against specific proto-oncogenes in the signal transduction pathway leading to the radiation resistant phenotype. More specifically, the method employs the administration of antisense oligonucleotides complementary to unique sequences of at least one of raf-1, Ha-ras, and HER-2 genes such that the expression of these factors is reduced, and the cells are radiosensitized.

Therefore, it is an object of the present invention to provide antisense oligonucleotides for reverting radiation and drug resistant cells in vitro and in vivo, for use in diagnostic assays for detecting expression of genes in the signal transduction pathway leading to radiation and/or drug resistance, and for use as therapeutic agents for inhibiting tumor cell growth to improve response to conventional therapeutics and therefore improve survival.

It is another object of the present invention to provide a method for decreasing raf-1, Ha-ras, or HER-2 expression important in reverting radiation resistant cells to radiation sensitive cells or to reduce symptoms of diseases resulting from the overexpression of these genes. For example, it is possible to inhibit restenosis, abnormal wound repair, or any biological activity which is produced by signaling through these pathways. These genes are involved in multiple signal transduction pathways, one of which, the MAPK pathway, is considered antagonistic to apoptosis. Perturbation of the signal transduction pathways by these antisense oligonucleotides may lead to or potentiate apoptosis. Ras signaling through the Ras/MAPK pathway may also play a role in formation of long-term memory and abnormal expression may therefore impact on disease states such as senility and Alzheimer's. Mutated Ras acting through a different signaling pathway, inhibits skeletal muscle differentiation. A mutation in a member of the raf family, A-raf, was found in mice to lead to neurological and gastrointestinal abnormalities and death in mice. Elevated levels of a fragment of HER-2 protein found in sera was considered a possible cause of pre-eclampsia or HELLP syndrome in pregnant women. Therefore, decreasing expression of these genes may be important in reversing or reducing these conditions and diseases.

It is a further object of the present invention to provide a method to resensitize radiation- and drug-resistant cells, the method comprising administering to the cells antisense oligonucleotides of genes identified in the signal transduction pathway leading to resistance such as oligonucleotides of the present invention. Other genes involved in the MAPK signal transduction pathway are defined in FIG. 6. Applicants have found that growth factor sis (PDGF-β), receptor tyrosine kinases trk (nerve growth factor), met (hepatocyte growth factor), tyrosine kinase src, serine/threonine kinase mos, protein kinase C β-1, nuclear oncogene ets-1, as well as some other components of the MAPK pathway, are involved in the radiation resistant phenotype, and administration of oligonucleotides which block the transduction pathway through these and other genes in this pathway may reduce the radiation resistance phenotype [Pirollo, K. F. et al. (1993) *Rad. Res.* 135:234–243]. This method is important in the treatment of tumors, especially tumors which have acquired resistance to radiation and drugs, both endocrine and chemical.

It is yet another object of the present invention to provide a method for inhibiting tumor growth by reducing levels of raf-1, Ha ras or HER-2 in said tumor, thereby resensitizing radiation- and drug-resistant cells in the tumour to radiation and drugs such that these cells can be treated again with either radiation or drugs.

It is still another object of the present invention to provide a method for detecting the level of raf-1, Ha-ras or HER-2 RNA in a cell comprising labeling the antisense oligonucleotides of the present invention and using the labeled oligonucleotides in a hybridization assay or a polymerase chain reaction (PCR) assay to detect the presence of the gene or amount of raf-1, Ha-ras and HER-2 RNA in a cell.

It is yet another object of the present invention to provide a therapeutic agent for treating diseases associated with an increase in raf-1, Ha-ras and HER-2, such as cancer, for example, the agent comprising the antisense oligonucleotides of the present invention in a pharmaceutically acceptable amount, in a pharmaceutically acceptable excipient.

It is further another object of the present invention to provide a method for visualizing raf-1, Ha-ras and HER-2 RNA in an organism, said method comprising labeling the antisense oligonucleotides of the present invention with a detectable label useful for imaging, and administering the labeled oligonucleotides at the site where imaging is desired, and detecting the label.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1A:
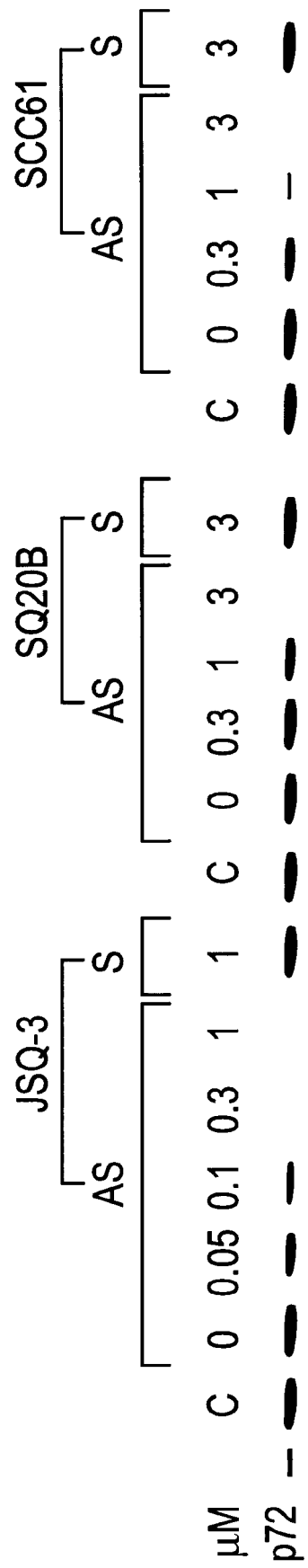
FIG. 1. The effect of anti-raf-1 oligonucleotides on Raf-1 p 72 protein synthesis and the radiation resistance levels of SCCHN cell lines JSQ-3 and SQ-20B. A—Western blot analysis of Raf-1 protein synthesis inhibition by increasing concentrations of raf-1 oligonucleotides. C=untreated cells; O=cells treated with liposomes but no oligonucleotides; AS=antisense; S=sense. B—Histogram demonstrating radiosensitization with increasing concentrations (0.1, 0.3, 1 $\mu$M) of anti-raf-1 ASO. As controls, the cells were treated with 1 $\mu$M of either a sense or a scrambled raf-1 oligonucleotide. Radioresistance levels are given as $D_{10}$ values. Error bars represent the standard error of the mean (S.E.M.) of 2 to 13 values.

As was discussed above, previous studies have indicated the presence of a signal transduction pathway leading to cellular radiation resistance. We hypothesized that inhibiting or reducing the expression of members of this pathway in cells should block signaling leading to decreased radioresistance. Members of this pathway include, but are not limited to, raf-1, Ha-ras and HER-2. One method for reducing the expression of these genes is through antisense oligonucleotides or ribozymes.

Therefore, in one embodiment, the present invention relates to a composition of matter consisting essentially of at least one antisense oligonucleotide substantially complementary to an RNA sequence (mRNA or pregenomic RNA) encoded by the raf-1 gene, preferably at or near the initiation codon of raf1, at about nucleotides 130 to 147, or around the promoter sequence or at single stranded loops based on secondary structure. The oligonucleotide is preferably comprising a sequence of at least about 8 nucleotides, is preferably not more than about 40 nucleotides, more preferably about 15–20 nucleotides, and optimally about 18 nucleotides.

The present invention also relates to antisense oligonucleotides substantially complementary to an RNA sequence (mRNA or pregenomic RNA) encoded by the Ha-ras gene, preferably at or near the initiation codon of Ha-ras, at about nucleotides 1670 to 1680, or alternatively, near a region of the gene where mutations causing activation are most prevalent, for example at codons 12 and 61. The oligonucleotide is preferably comprising a sequence of at least about 8 nucleotides, is preferably not more than about 40 nucleotides, more preferably about 15–20 nucleotides, and optimally about 11 nucleotides.

The present invention also relates to antisense oligonucleotides substantially complementary to an RNA sequence (mRNA or pregenomic RNA) encoded by the HER-2 gene, preferably at or near the initiation codon of HER-2, at about nucleotides 708 to 718, or around the promoter sequence or at single stranded loops based on secondary structure. The oligonucleotide is preferably comprising a sequence of at least about 8 nucleotides, is preferably not more than about 40 nucleotides, more preferably about 15–20 nucleotides, and optimally about 11 nucleotides As used herein, "substantially complementary" means that an antisense oligonucleotide of the invention is capable of hybridizing with its RNA target under physiological conditions, e.g., as pertains inside a cell expressing raf-1. Since there is substantial homology between the raf-1 family members, it is possible to use sequences from other family members as antisense nucleotides or to design other antisense sequences in order to inhibit their gene expression. Whether or not a sequence is substantially complementary can be determined by techniques known to those with ordinary skill in the art. For example, the sequence of the antisense oligonucleotide can be compared to the raf-1 sequence in EMBL databank, accession no. X03484, [Bonner, T. J. (1986) *Nucl. Acids Res.* 14:1009–1015], to the Ras sequence VOO574, J00276, J00277, K00954 [Capon, D. J. (1983) *Nature* 302: 33–37] and to the HER-2 sequence [Coussens, L. (1985) *Science* 230: 1132–1138] and its ability to hybridize to RNA under appropriate stringency conditions can be determined. Hybridization techniques are known in the art. See for example, *Current Protocols in Molecular Biology*, John Wiley & Sons, New York, N.Y.

As used herein, "consisting essentially of" has its usual meaning, i.e., that one or more compositions of matter of the invention may be used together, either in admixture or combined in a single molecule, with other materials that do not alter the essential nature of the invention. For example, while the antisense oligonucleotide sequences of the invention are essential to the invention, it is contemplated that they may be used in admixture or in chemical combination with one or more other materials, including other oligonucleotides, materials that increase the biological stability of the oligonucleotides, or materials that increase their ability to selectively penetrate their target cells and reach and hybridize to their target RNA. Furthermore, the term "oligonucleotide" includes derivatives thereof, such as backbone modifications, e.g., phosphorothioate derivatives, employed to stabilize the oligonucleotide. All such modifications are contemplated equivalents of the antisense oligonucleotides of the invention. The following discussion provides examples of the kinds of modifications that may be employed, but those of skill in the art will readily recognize others. Non-naturally occurring backbones carrying bases and capable of base pairing to natural nucleic acids both known and not as yet invented, may be substituted for DNA or RNA oligonucleotides; such backbones may prove more stable than DNA or RNA. For example, the antisense oligonucleotides may be provided in stabilized form, e.g. with phosphotriester linkages, or by blocking against exonuclease attack with methylphosphonodiester linkages, with 3' deoxythymidine, as a phenylisourea derivative, or by linking other molecules such as aminoacridine or polylysine to the 3' end of the oligonucleotide. See e.g., *Anticancer Research* 10: 1169–1182, at 1171–2 (1990), the teaching of which is incorporated herein by reference. Though exemplified herein by single-stranded DNA molecules, it will be recognized that non-DNA backbones may be substituted. For instance, an RNA or RNA-DNA hetero-oligomer antisense molecule would be useful if one desired the antisense sequence be less stable or more tightly binding than a DNA oligonucleotide. Base analogues may be substituted for the commonly found A (adenosine or deoxyadenosine), G (guanosine or deoxyguanosine), C (cytidine or deoxycytidine), T (thymine) or U (uridine). Examples include, but are not limited to, 7-aza-G and 5-methyl-C. Such base analogues are useful for adjusting Tm of an oligonucleotide or a segment thereof. Tm, or melting temperature, is a measure of binding between two strands of a double-stranded nucleic acid. Substitution of rT (ribothymidine) for U or dU (deoxyuridine) for T are also possible. Other strategies include attaching oligonucleotides to DNA-protein complexes or cationic liposomes as exemplified in the Examples following. For antisense oligonucleotides supplied exogenously, increased selectivity for cell type may be achieved by linking antisense oligonucleotide complexes of the invention to natural ligands of the target cell or cell-specific antibodies, or to synthetic ligands that will bind to the target cell. The oligonucleotide may also be at least partially double stranded, either by binding to a distinct oligonucleotide or by formation of a hairpin, either at one or both termini or internally as long as the oligonucleotide is still able to decrease expression of the desired gene in a cell.

The present invention is not limited to any particular method of making the antisense oligonucleotides. The antisense oligonucleotides may be produced by any method known to the art. While those exemplified herein were synthesized using an automated synthesizer, expressed nucleotides made by an expression vector used for gene therapy, such as an adenoviral, retroviral, or plasmid vector can be designed to produce antisense RNA when introduced into a cell. Use of other synthetic chemistries is possible, see for example, Ulhmann and Peyman (1990) *Chemical Rev.* 90: 544–584. Other methods of making these oligonucleotides will be evident to those with skill in the art. It will be recognized by those in the art that having shown that the invention is operative with the exemplified oligonucleotides and in accordance with other teachings of the present invention, those of ordinary skill in the art are enabled to design and test oligonucleotides not exemplified herein, that are also operative.

In another embodiment, the present invention relates to compounds for use in the treatment or diagnosis of disease. The compounds of the present invention are antisense oligonucleotides as described above, able to reduce the expression of the gene they target, specifically, raf-1, Ha-ras or HER-2. The compounds of the present invention can be used as therapeutic agents to treat or diagnose disorders or diseases related to the expression of raf-1, Ha-ras or HER-2. Such diseases include but are not limited to, cancer, restenosis, osteoarthritis, neurological and intestinal abnormalities, pre-eclampsia, among others.

The compounds of the present invention may be used to detect the level or presence of raf-1, Ha-ras or HER-2 RNA or DNA in a sample, said sample being a cell, cell extract, purified DNA or RNA from cells, tissue, or organ, or sections of tissues or organs, or diagnose an increase in raf-1, Ha-ras or HER-2 RNA in a cell, by detecting raf-1, Ha-ras or HER-2 RNA. The level of raf-1, Ha-ras or HER-2 RNA can be detected by extracting cellular RNA and detecting the level of raf-1, Ha-ras or HER-2 RNA using a hybridization assay, such as a Northern hybridization assay wherein the antisense oligonucleotides are labeled with a detectable label, or alternatively, by in situ assay of a cell or organ or tissue section using in situ hybridization techniques known to persons in the art. In addition, the compounds of the present invention can be used in a polymerase chain reaction assay as primers for the detection of raf-1, Ha-ras or HER-2 RNA or DNA in cells by methods well known in the art. The compounds of the present invention may be labeled using any of a variety of labels and method of labeling. Examples of types of labels which can be used in the present invention include, but are not limited to, enzyme labels, radioisotopic labels, non-radioactive isotopic labels, fluorescent labels, and chemiluminescent labels. Such assays may also be useful for in vitro testing of potential drugs for treating a disease involving raf-1, Ha-ras or HER-2 RNA, such as cancer, or to monitor the effect of the drug on raf-1, Ha-ras or HER-2 RNA expression. Cell lines useful for in vitro drug testing would be those expressing raf-1, Ha-ras or HER-2 RNA. For instance, cells expressing Ras include, but are not limited to,T24, Hs578T, SK-CO-1, Calu1 among others [Bos, J. L. (1988) *Mutation Research* 195: 255–271]; Cells expressing Raf-1 include, but are not limited to, SQ-20B, JSQ-3 and other SCCHN cell lines, among others [Weichselbaum, R. R. et al. (1988) *Int. J. Radiation Oncology Biol. Phys.* 15: 575–579; Weichselbaum, R. R. et al. (1986) *PNAS USA* 83: 2684–2688]. Cells expressing HER-2 include, but are not limited to SK-OV-3, ZR-75-1, MDA-MB-435, and MDA-MB-453, among others.

As was discussed above, a signal transduction pathway, with raf-1, Ha-ras or HER-2 as central elements, leads to cellular drug resistance and radioresistance. Chemotherapy and radiation are two major forms of adjuvant therapy for various types of cancer. The ability to revert drug/radiation resistant tumor cells thereby rendering them drug/radio-sensitive and vulnerable to drug and radiation treatments, provides a valuable method in the treatment of tumors. The antisense oligonucleotide compositions of the present invention are able to ameliorate or revert the drug resistance and radioresistance of tumor cells. Raf-1 expressing tumors include stomach, and squamous cell carcinoma of the head and neck (upper aero-digestive track); ras expressing tumors include bladder, breast, lung, colon, pancreas, prostate; HER-2 expressing tumors include breast, ovarian, cervical, lung, prostate, head and neck cancers.

The oligonucleotides can be used in a method for treating diseases or conditions involving raf-1, Ha-ras or HER-2 expression, or where the modulation of these genes is desired. The method would include administering an effective amount of one or more of the compounds of the present invention, or one or more raf-1, Ha-ras or HER-2 antisense oligonucleotide(s) to a patient requiring such a treatment, such that the level of the targeted RNA or protein is decreased. The antisense oligonucleotides can be prepared for administration by methods known in the art which can include filtering to sterilize the solution of antisense oligonucleotides, diluting or concentrating the solution, adding a stabilizer to the solution, lyophilizing the solution to produce the oligonucleotides in dried form for ease in transportation and storage. Improvement of oligonucleotide uptake has been achieved with different systems of vectorization including liposomes (neutral, cationic, immunoliposome), nanoparticles, or covalent attachment of a carrier. Advantageously, the antisense oligonucleotides are combined with "sterically stabilized" liposomes (S-liposomes) which have been developed and are suitable for therapeutic applications such as sustained drug release and selective delivery of drugs to specific targets [Reviewed in Allen, T. M. (1994) *TIPS* 15, 215–220 and Gregoriadis, G. and Florence, A. T. (1993) *Drugs* 45: 15–28]. Long circulating half-lives and the ability of the S-liposomes to localize in high concentration in solid tumors make them useful in cancer treatment. The liposome-antisense delivery can be passive for example by simple fusion with the cell, or active by attachment of antibodies or other proteins to the liposome surface to cause specific targeting [Allen, T. M. et al. (1994) *J. Lipos. Res.* 4: 1–25; Mori, A. et al. (1991) *FEBS Lett.* 284: 263–266]. Further, the antisense oligonucleotide treatment solution can be in the form of a mixed solution which contains the antisense oligonucleotides described above and at least one other antigen or oligonucleotide, as long as the added compound does not interfere with the effectiveness of the antisense oligonucleotide treatment and adverse reactions such as toxicity are not increased additively or synergistically.

The antisense oligonucleotide treatment solution may be stored in a sealed vial, ampule or the like. The present treatment can be administered in the form of a spray for intranasal administration, or by nose drops, inhalants, eye drops, skin patch, suppository, mini-pump implant, or a capsule, liquid suspension or elixirs formulated for oral administration. In the case where the treatment is in dried form, the treatment can be dissolved or suspended in sterilized distilled water or saline before administration. Any inert carrier is preferably used, such as saline, phosphate buffered saline, or any such carrier in which the antisense oligonucleotides have suitable solubility.

Generally, the method of administration of treatment may depend on the organ or organs targeted. The compounds or treatment may be administered orally, subcutaneously, intravenously, or intramuscularly or intracranially by direct injection. For example, in the lung, the composition would be administered as an inhalant, or intravenously; in the breast, head or neck, intravenously or direct injection; in the bladder, ovaries, or pancreas, intravenously. These methods of administration are known to people in the art.

The compounds of the present invention can be administered in a dose effective for the production of a decrease in raf-1, Ha-ras or HER-2 and resulting in an improvement of the patient's disease, or amelioration of the patient's disease symptoms. The treatment may be in the form of a single dose or in multi-dose program. At low (sub-optimal) concentrations of the oligonucleotides, the effect may be additive or even synergistic. When providing a patient with antisense oligonucleotides, the dosage administered will vary depending upon such factors as the patient's age, weight, height, sex, general medical condition, previous medical history, etc. In general, it is desirable to provide the recipient with a dosage of the above compounds which is in the range of 1 pg/kg to 500 mg/kg (body weight of patient), although a lower or higher dosage may be administered.

Described below are examples of the present invention which are provided only for illustrative purposes, and not to limit the scope of the present invention. Other suitable modifications and adaptations of the variety of conditions and parameters normally encountered in this art which are obvious to those skilled in the art are within the spirit and scope of the present invention.

The following MATERIALS AND METHODS were used in the examples that follow.

Oligonucleotides

Phosphorothioated ASO directed at or near the initiation codon were synthesized by Midland Certified Reagent Co., Midland, Tex. for the raf-1 (5'-TCCCTGTATGTGCTCCAT-3')(SEQ ID NO:1), Ha-ras (5'-TATTCCGTCAT-3') (SEQ ID NO:2), and HER-2 (5'-TCCATGGTGCTCACT-3') (SEQ ID NO:3) genes.

Two controls for each gene, either a sense and a scrambled (for raf-1) or two different scrambled (for Ha-ras and HER-2) oligonucleotides were also synthesized. The scrambled oligomers have the same base composition as antisense but in a different, random order. The sequences for the raf-1 controls are 5'-ATGGAGCACATACAGGGA-3' (sense) (SEQ ID NO:4) and 5'-CTAGCCTATCTGTCTTCG-3' (scrambled) (SEQ ID NO:5); for Ha-ras 5'-TTATACGTCCT-3' (scrambled 1) (SEQ ID NO:6) and 5'-TTATACGTCCT-3' (scrambled 2) (SEQ ID NO:7); and for HER-2 5'-CACTGGTTGCACCTT-3' (scrambled 1) (SEQ ID NO:8) and 5'-CTAGCCATGCTTGTC-3' (scrambled 2) (SEQ ID NO:9).

Cell Culture and Treatment

Squamous cell carcinoma of the head and neck (SCCHN) cell lines JSQ-3 (Weichselbaum R. R., et al. (1988) *Int. J. Radiation Oncology Biol. Phys.* 15:575–579), SQ-20B (Weichselbaum R. R., et al. (1986) *Proc. Natl. Acad. Sci. USA* 83:2684–2688) and SCC-61 (Weichselbaum R. R., et al. (1986) *Proc. Nail. Acad. Sci. USA* 83:2684–2688), which were kind gifts from Dr. Ralph Weichselbaum, University of Chicago, were maintained in Minimum Essential Medium with Earle's salts (EMEM), supplemented with 10% heat inactivated fetal bovine serum; 50 µg/ml each of penicillin, streptomycin and neomycin; 2 mM L-glutamine; 0.1 mM non-essential amino acids, 1 mM pyruvate and 0.4 µg/ml hydrocortisone. Human ovarian (SK-OV-3) and bladder (T24) carcinoma cell lines (obtained from ATCC, Rockville, Md.) were maintained in McCoy's 5A medium supplemented with 10% fetal bovine serum, 50 µg/ml each of penicillin, streptomycin and neomycin and 2 mM L-glutamine. Normal human non-tumor breast cell line MCF 10A (ATCC, Rockville, Md.) was maintained in a 1:1 mixture of Dulbecco's modified Eagle's medium and Ham's F12 medium supplemented with 5% horse serum, 20 ng/ml epithelial growth factor, 100 ng/ml cholera toxin, 0.01 mg/ml insulin, 500 ng/ml hydrocortisone, 50 µg/ml each of penicillin, streptomycin and neomycin and 2 mM L-glutamine.

For oligonucleotide treatment, the cells were plated at $1 \times 10^5$ cells/well in 6-well tissue culture plates. Twenty-four hours later, at approximately 40–60% confluency, the cells were transfected with the oligonucleotides, facilitated by Lipofectin Reagent, using essentially the protocol supplied by the manufacturer, Life Technologies, Inc. After 6 hours, the lipofection solution was removed and the monolayer washed with fresh medium containing 8 mM L-glutamine and 20% serum. The cells were then incubated for an additional 16–18 hours in 1 ml of this medium.

Radiobiology

Cellular response to radiation was evaluated by the colony survival assay. Exponentially growing monolayer cultures of each cell line were treated with the oligonucleotides as described above. The cells were harvested 24–48 hours later, suspended in fresh medium and irradiated at room temperature with graded doses of $^{137}$Cs γ rays at a dose of approximately 36 Gy/minute in a J. L. Shepard and Associates Mark I irradiator. Afterward, the cells were diluted and plated at a concentration of 300 to 5000 cells per well in a 6-well tissue culture plate. Two to three days after plating, the cells were supplemented with 0.5 ml of serum plus 5 µg/ml hydrocortisone. Approximately 7–14 days later, the cells were stained with 1% crystal violet and colonies (comprising 50 or more cells of normal appearance) were scored. Survival curves were plotted as the log of the survival fraction versus the radiation dose using Sigma-Plot Graphics program. $D_{10}$ (the dose required to reduce survival to 10%) values were calculated from the initial survival data.

Protein Analysis

After oligonucleotide treatment, cells for protein analysis were trypsinized, pelleted, rinsed with PBS and lysed in RIPA buffer (1% NP40, 0.5% sodium deoxycholate, 0.1% SDS, 30 μg/ml aprotinin and 1 mM sodium orthovanidate in PBS) (Santa Cruz Biotechnology, Inc). After shearing with a 26 gauge needle, 100 μg/ml Phenylmethylsulfonyl fluoride (PMSF) was added, the lysate incubated on ice for 30–60 minutes and centrifuged at 13,000×g for 20 minutes at 4° C. to pellet insoluble material. Protein concentration was determined using the micro-BCA Protein Assay Kit (Pierce Biochemicals).

Protein lysate (40 μg for Ha-ras, 5 μg for raf-1 and HER-2) was mixed with an equal volume of 2× protein sample buffer (0.05 M Tris (pH 6.8), 3% SDS, 20% Glycerol, 6% 2-Mercaptoethanol and 0.001% Bromophenol blue) boiled for 5 minutes, loaded on a 12% (5% stacking gel) SDS/Polyacrylamide gel and electrophoresed at 200V for 8 hours. The protein was transferred to nitrocellulose membrane as previously described [Janat, M. F. et al. (1994) *Mol. Cell. Diff.* 2:241–253]. Preparation of membrane and incubation with the primary and secondary antibodies was performed essentially as described in a protocol supplied by Santa Cruz Biotechnology, Inc., with the exception that incubation with the primary antibody was extended to 1 hour for raf-1, 2 hours for HER-2 and 4 hours for Ha-ras and wash times of 15 minutes per wash were used. The primary antibodies for HER-2 (neu C-18) and Ha-ras (ras C-20) were obtained from Santa Cruz Biotechnology, Inc. The anti-raf-1 antibody was a kind gift from Dr. Andrew Laudana, University of Vermont [McGrew, B. R. et al. (1992) *Oncogene* 7: 33–42]. The washings after addition of the secondary antibody (Anti-mouse IgG-HRP, Santa Cruz Biotechnology, Inc.) were also lengthened to 15 minutes per wash.

Visualization of the protein was accomplished using the ECL Chemo-luminescent Western Blotting Kit (Amersham) according to the manufacturer's protocol.

EXAMPLE 1

Human tumor cell lines JSQ-3 and SQ-20B, which display a high level of radiation resistance, were established from SCCHN tumors which failed radiotherapy [Weichselbaum, R. R. et al. (1988) supra; Weichselbaum, R. R. (1986) supra]. An activated form of the raf-1 oncogene was isolated from these cell lines via the NIH 3T3 transfection assay [Kasid, U. et al. (1987) *Science* 237: 1039–1041]. These and other studies with radioresistant non-cancerous skin fibroblast cell lines from a cancer-prone family [Chang, E. H. et al. (1987) *Science* 237: 1036–1039; Pirollo, K. F. et al. (1989) *Int. J. Radiat. Biol.* 55: 783–796] have clearly linked activation of raf-1 to increased RR. We, therefore, wished to determine if treatment of these cell lines with anti-raf-1 ASO would inhibit raf-1 expression and revert this phenotype. Consequently, JSQ-3 and SQ-20B were treated with increasing concentrations of anti-raf-1 oliogonucleotides and the level of the raf-1 protein expression determined. Since we have previously shown that lipofectin enhanced uptake of these compounds resulting in lower effective doses, a commercially available liposome preparation (Lipofectin) was used in these and all subsequent experiments to facilitate delivery of the oligonucleotides. As shown in FIG. 1A, Raf-1 protein expression in JSQ-3 cells is completely inhibited by treatment with 1 μM of antisense raf-1, with significant inhibition evident at a concentration as low as 0.1 μM. The specificity of the inhibition was demonstrated by treating the cells with Lipofectin alone (0) or with a raf-1 sense oligonucleotide (S). No decrease in protein expression as compared to the untreated control cells (C) was observed in either case. A similar pattern of results was observed with cell line SQ-20B. However, with this cell line, a 3 μM concentration was necessary to effect complete inhibition of raf-1 protein, with only approximately 50% inhibition observed at 1 μM. Also shown in FIG. 1A is the effect of raf-1 ASO on a radiosensitive SCCHN cell line, SCC61. Here also treatment with raf-1 ASO was able to specifically inhibit raf-1 protein expression.

EXAMPLE 2

Figure 1B:
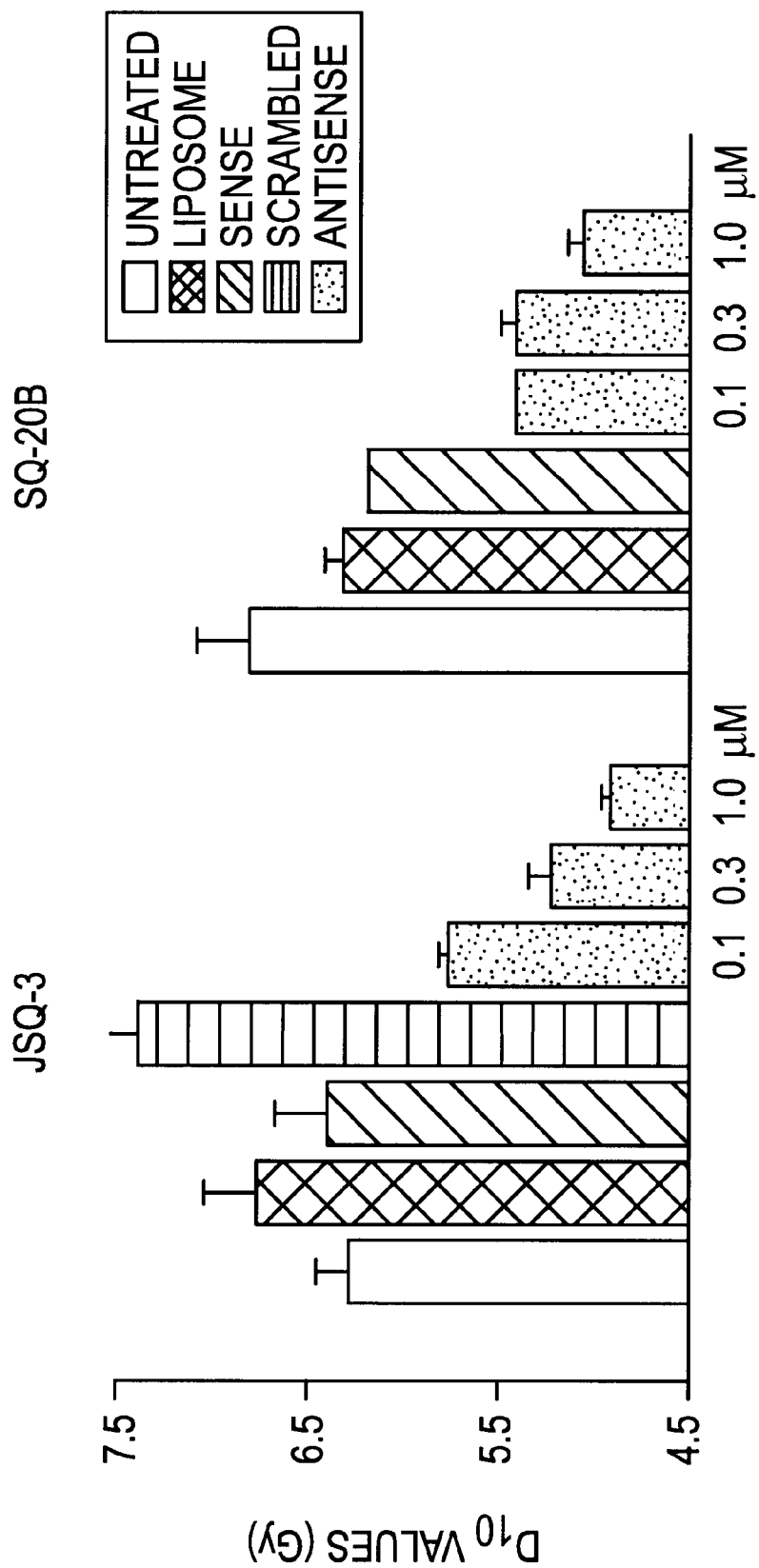

We next examined the effect of anti-raf-1 on the RR level of these cells. FIG. 1B demonstrates a dramatic increase in radiosensitivity for both cell lines after ASO treatment. This response, particularly in the JSQ-3 cells, is dose dependent. The $D_{10}$ value for JSQ-3 drops from the highly resistant level of 6.3±0.16 Gy to 4.9±0.05 Gy, a value much closer to the level considered to be radiosensitive, after treatment with 1 μM raf-1 ASO. Even a dose as low as 0.3 μM is capable of significantly sensitizing these cells to killing by γ-radiation. Similarly, the resistance level of SQ-20B is reduced from 6.8±0.31 Gy to 5.1±0.09 Gy. This change of approximately 1.5 Gy was found to be highly statistically significant ($p<0.001$). Here also, the specificity of the oligonucleotide is evident since treatment with either Lipofectin (Liposome) alone, a sense, or a scrambled oligomer had minimal or no effect on the RR level of the cells. Moreover, the differences between JSQ-3 and SQ-20B with respect to their level of sensitization after ASO treatment correlates with that observed in the protein analysis, indicating that this decrease in radioresistance is directly related to Raf-1 expression. An example of the survival curves produced in these experiments is given as FIG. 2A.

By contrast, treatment of SCC61 cells, which are highly radiosensitive, with 1 μM of raf-1 ASO had no significant effect on their radiation response level. The $D_{10}$ value of the control and sense treated cells was found to be 3.3±0.4 Gy and 3.4±0.06 Gy, respectively, while that of the ASO treated was 3.0±0.4 Gy indicating a slight, but not significant, sensitization of the cells by the raf-1 ASO.

EXAMPLE 3

Figure 2:
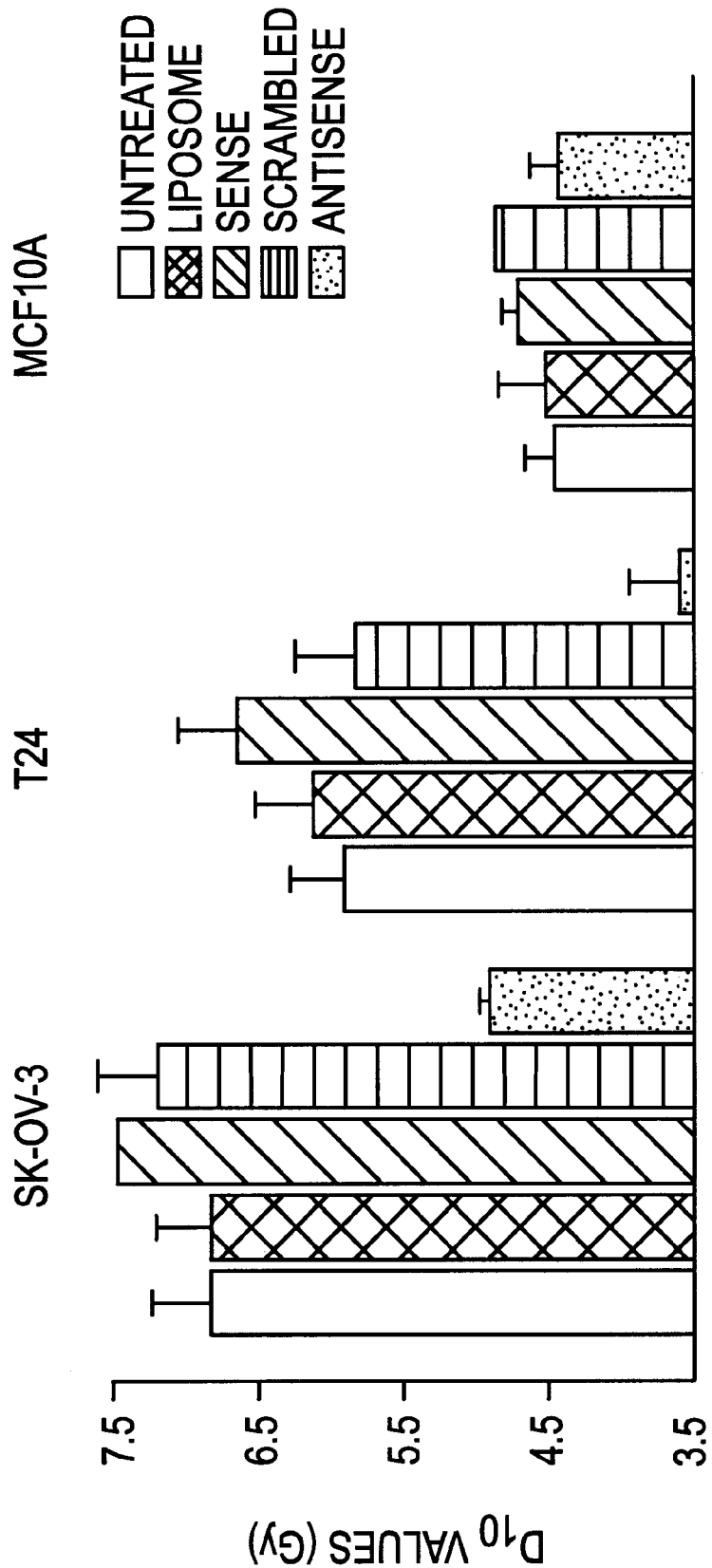
FIG. 2. Histogram demonstrating the effect of 1 $\mu$M anti-raf-1 ASO on SK-OV-3, T24 and MCF10A cells. As controls, the cells were treated with 1 $\mu$M of either a sense or a scrambled raf-1 oligonucleotide. Radioresistance levels are given as $D_{10}$ values. Error bars represent the S.E.M. of 2–6 values.
Figure 3B:
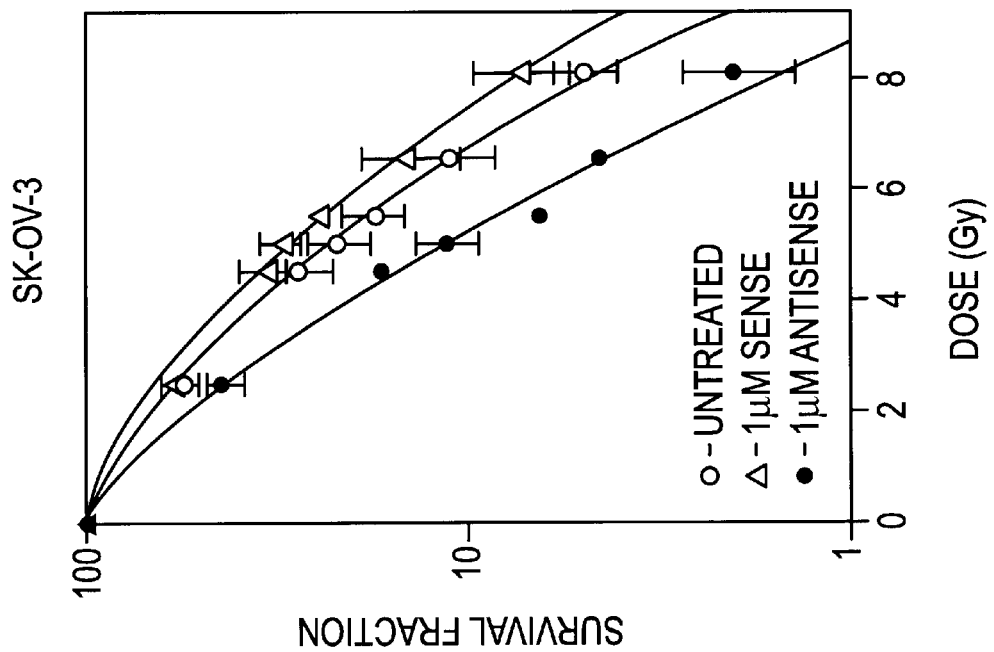
FIG. 3. Survival curves, after graded doses of γ-radiation, for A—JSQ-3 and B—SK-OV-3 cells untreated or treated with either 1 $\mu$M raf-1 antisense or sense oligonucleotides. Curves are plotted as the log of the surviving fraction vs. radiation dose in Gy. Points are plotted as the S.E.M. of 2–13 values.
Figure 3A:
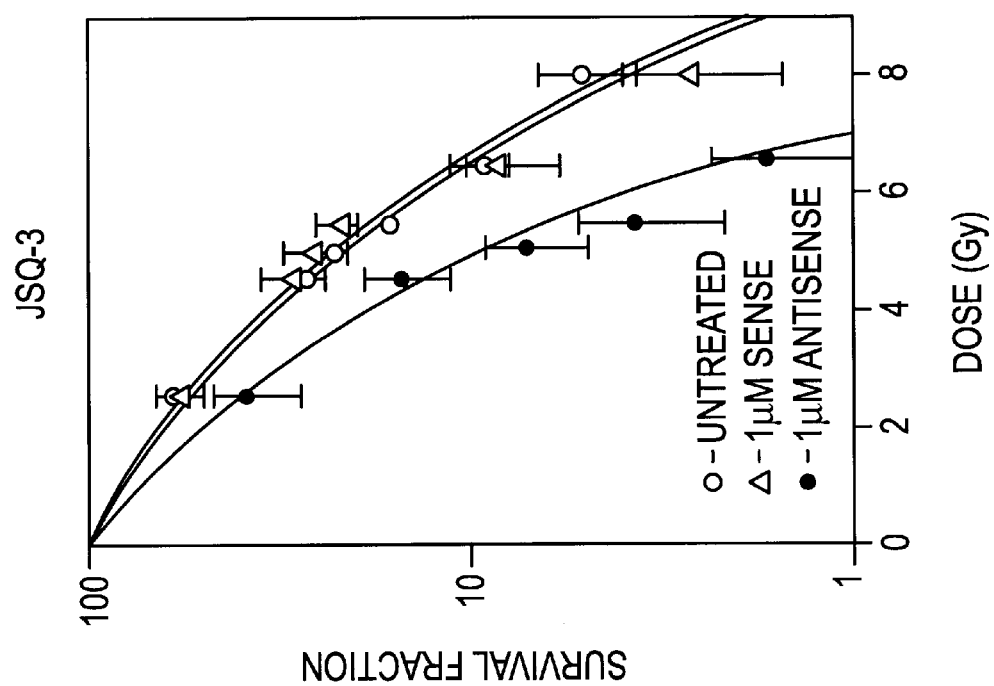

Our previous studies have placed raf-1 in a central role in a proposed signal transduction pathway leading to cellular RR. If this hypothesis is correct then treatment with raf-1 ASO of cells which have activated or abnormally expressed genes upstream of raf-1 in this pathway should block signaling leading to decreased radioresistance. Therefore, we transfected human tumor cell lines SK-OV-3 and T24 with raf-1 ASO. These two cell lines possess either elevated levels of HER-2 [Chan, S. D. et al. (1995) *J. Biol. Chem.* 270: 22608–22613] or a mutated Ha-ras genes [Tabin, C. J. et al. (1982) *Nature* 300: 143–149], respectively. Both of these genes have been placed upstream of raf-1 in the signal transduction pathway [Daum, G. et al. (1994) *TIBS* 19: 474–480; Rapp, U. R. et al. (1988) The Oncogene Handbook (T. curran, J. E. P. Reddy, and A. Skala, Eds.) pp. 213–252, Elsevier, Amsterdam]. The presence of 1 μM antisense raf-1 was able to significantly reduce the RR level of both cell lines from 6.83±0.42 Gy to 4.90±0.08 Gy for SK-OV-3 and from 5.93±0.36 Gy to 3.58±0.36 Gy for T24 (FIG. 3). As before, treatment with either the sense or scrambled oligo did not decrease on the RR level of the cells. This sensitization is also evidenced by the differences in the survival curves between control SK-OV-3 cells, and those treated with 1 uM raf-1 antisense oligonucleotides (FIG. 2B). As a control, a normal radiosensitive breast epithelial cell line, MCF10A, was also used. As with SCC61, no effect on the $D_{10}$ values was observed with this cell line, again indicating no further sensitization of the cells at this concentration of ASO.

EXAMPLE 4

Figure 4:
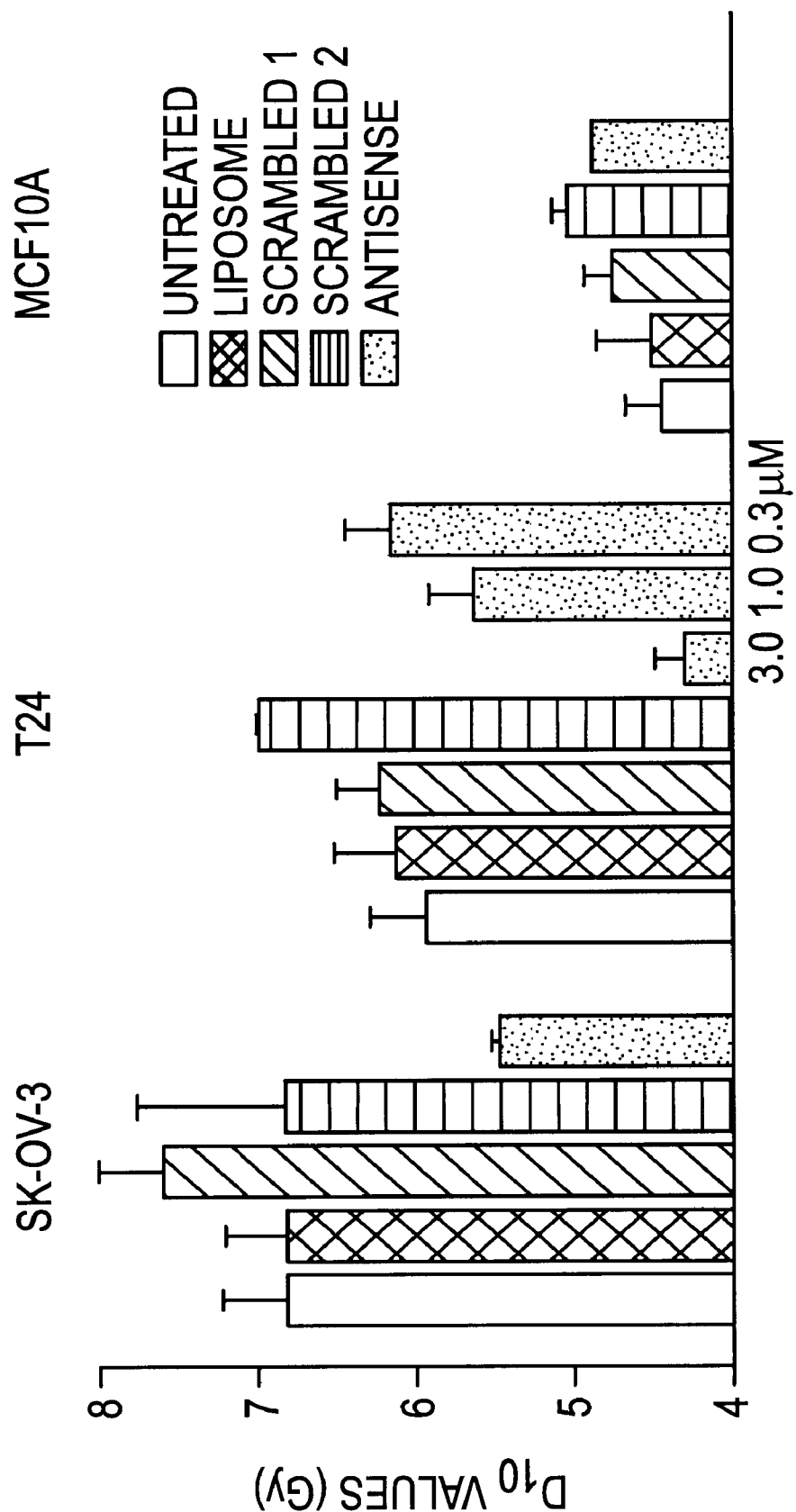
FIG. 4. Histogram demonstrating radiosensitization by Ha-ras ASO. The concentration of antisense ras oligonucleotide used to treat SK-OV-3 and MCF10A was 3 μM. As controls, the cells were treated with 3 μM of two different scrambled Ha-ras oligonucleotides. Radioresistance levels are given as $D_{10}$ values. Error bars represent the S.E.M. of 2–7 values.

To further confirm the role of these activated oncogenes in signal transduction and the RR phenotype, SK-OV-3, T24 and MCF10A cells were also treated with ASO against the Ha-ras gene. Since, as a growth factor receptor, HER-2 is upstream of ras in the proposed signalling pathway, it would be expected that the Ha-ras ASO would affect both the HER-2 expressing cells (SK-OV-3), and the cells containing mutant Ha-ras (T24). FIG. 4 shows this to be the case. $D_{10}$ for the 3 µM ASO treated T24 cells is decreased from the control value of 5.93±0.36 Gy to the significantly more radiosensitive value of 4.29±0.20 Gy, while that for SK-OV-3 is lowered from 6.83±0.42 Gy (Control) to 5.47±0.03 Gy after introduction of the anti-ras molecule. As before, there was no significant decrease in radiation survival in the control MCF10A cells after ASO treatment.

EXAMPLE 5

Figure 5A:
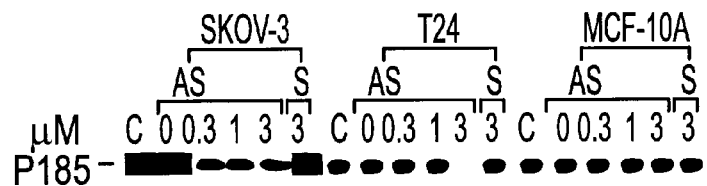
FIG. 5. The effect of anti-HER-2 oligonucleotides on p185 HER-2 protein synthesis and the radiation resistance levels of SK-OV-3, T24 and MCF10A cells. A—Western blot analysis of HER-2 protein synthesis inhibition by increasing concentrations (0.3, 1.0 & 3.0 μM) of HER-2 oligonucleotides. C=untreated cells; O=cells treated with liposomes but no oligonucleotides; AS=antisense; S=scrambled. B—Histogram demonstrating radiosensitization by HER-2 ASO. The concentration of antisense HER-2 oligonucleotide used to treat T24 and MCF10A was 1 μM. As controls, the cells were treated with 1 μM of two different scrambled HER-2 oligonucleotides. Radioresistance levels are given as $D_{10}$ values. Error bars represent the S.E.M. of 2–7 values.
Figure 5B:
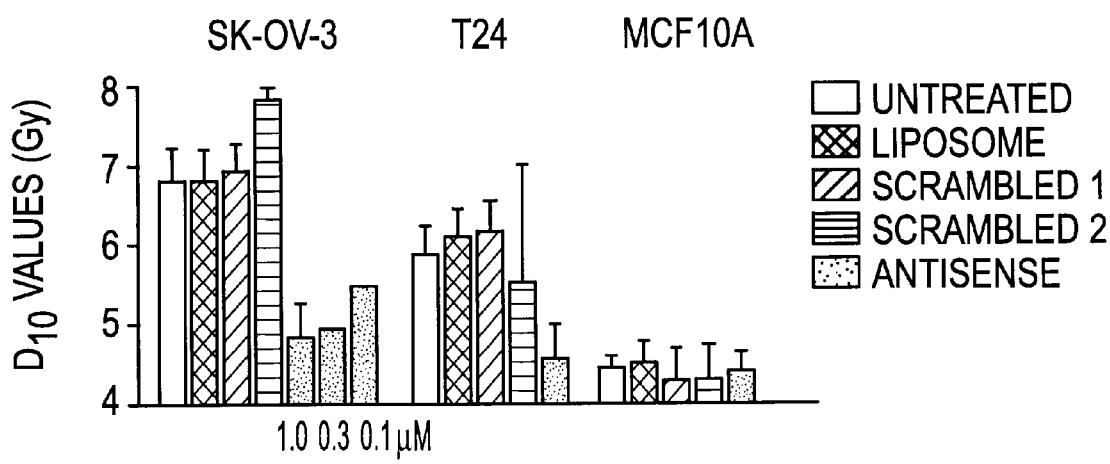
Figure 6:
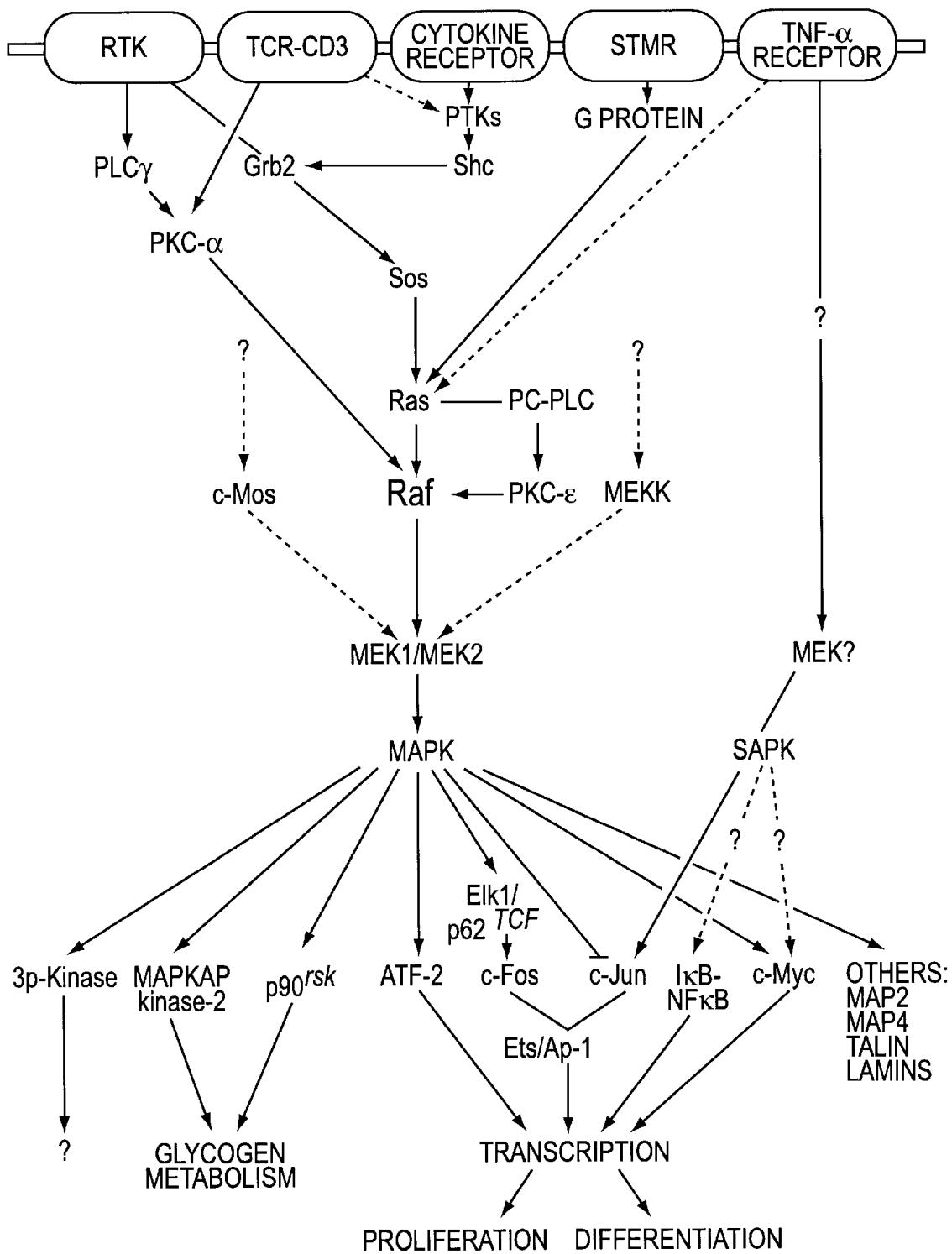
FIG. 6. Raf-dependent signal transduction. For clarity, additional pathways, such as JAK/STAT-mediated signalling, are omitted, as are feedback phosphorylation reactions. Raf is activated upon stimulation of a variety of receptors. Together with MAP/ERK kinase (MEK) and mitogen-activated protein kinase (MAPK; also known as extracellular-receptor-activated protein kinase, ERK) it forms the highly conserved cytoplasmic kinase cascade. MAPK acts on numerous effector molecules, such as other serine/threonine kinases or transcription factors, which finally determine the cellular response. Taken from Daum, G. et al. (1994) *Trends in Biochemical Sciences* 19:474–480.

These same three cell lines were also treated with antisense oligonucleotides directed against HER-2. Over 80% inhibition of HER-2 protein was observed in the SK-OV-3 cells with HER-2 ASO at a concentration as low as 0.3 µM (FIG. 5A). However, significant HER-2 protein inhibition in the T24 cells is found only at 3 µM and none is evident in MCF10A, even at this relatively high concentration of ASO. The effect of HER-2 ASO on the RR level of these cells was also examined (FIG. 5B). While treatment with 0.1 and 0.3 µM HER-2 ASO had some effect on the radiosensitivity of the SK-OV-3 cells, treatment with 1 µM HER-2 ASO significantly sensitized the SK-OV-3 cells, reducing the $D_{10}$ value from 6.83±0.42 Gy to 4.88±0.43 Gy, a result virtually identical to that observed after treatment of SK-OV-3 cells with 1 µM anti-raf-1 ASO. This change of approximately 2 Gy is highly statistically significant (p<0.001) and represents a 5 fold increase in sensitivity to radiation killing these cells. Surprisingly, the radiosensitivity of the T24 cells was also altered by treatment with 1 µM HER-2 ASO.

Discussion

In our previous studies we examined the relationship between activation of oncogenes and the phenomenon of cellular radiation resistance [Pirollo, K. F. et al. (1993) Rad. Res. 135: 234–243; Pirollo, K. F. et al. (1989), supra]. We proposed, based upon our findings and those of other researchers, the presence of a signal transduction pathway, analogous to that for cell growth and differentiation, leading to radiation resistance to killing by ionizing radiation [Pirollo, K. F. et al. (1993), supra]. In the studies described above, we present evidence confirming such a pathway. Activation of the raf-1 gene has been shown to be related to radiation resistance in SCCHN and in the non-cancerous skin fibroblasts from a cancer-prone family with Li-Fraumeni syndrome [Kasid, U. et al (1987), supra; Chang, E. H. et al. (1987), supra; Pirollo, K. F. et al. (1989), supra; Kasid, U. et al. (1989) Cancer Res. 49: 3396–3400]. Raf-1 is also known to play a central part in signal transduction via the MAP Kinase pathway [Campbell, J. S. et al. (1995) Recent Progress in Hormone Research 50: 131–159; Daum, G. et al. (1994), supra]. In this Ras/Raf/MEK/ERK pathway, a small guanine nucleotide-binding protein links receptor tyrosine kinase activation to a cytosolic protein kinase cascade [Marshall, C. J. (1995) Cell 80: 179–185].

The protein-protein interaction between Ras and Raf, through the CRI region on Raf-1 and the effector site of Ras, leads to a partial activation of Raf-1. Full activation of Raf-1 is achieved by another tyrosine kinase generated signal [Marshall, C. J. (1995), supra; Fabian, J. R. et al. (1994) PNAS USA 91: 5982–5986] and leads to the phosphorylation and activation of MEK, its only known physiological substrate. This in turn results in the activation of ERK1 and/or ERK2. The substrates for the ERKs in the nucleus are transcription factors, activation of which can set in motion a wide range of events. Raf-1 has also been shown to be a key component in the mammalian response to damage by ultraviolet light [Devary, Y. et al. (1992) Cell 41:1081–1091; Radler-Pohl, A. et al. (1993) EMBO J. 12: 1005–1012]. This "U.V. response" has been proposed to have a protective function, in a manner analogous to that of the bacterial "SOS" system. It was shown by Devary et al. that this pathway originates at the cell membrane and includes activation of Src, and Ha-Ras as well as Raf-1 in a signaling cascade leading to activation of transcription factor AP-1 and nuclear factor kappa B [Devary, Y. (1992), supra].

Protooncogenes and their oncogenic counterparts such as HER-2 (a homologue to an epidermal growth factor receptor) and ras are known to be upstream of raf-1 in the Map Kinase pathway [Daum, G. (1994), supra; Rapp, U. R. et al. (1988),supra]. The ability, as demonstrated here, of antisense oligonucleotides directed against raf-1 to revert the RR phenotype of cells containing activated ras or overexpressing HER-2 is clear evidence of signaling through raf-1 leading to RR. This is further supported by the ability of antisense ras oligomers to sensitize HER-2 overexpressing SK-OV-3 cells to γ-radiation killing. Although HER-2 is upstream of ras in the signal transduction pathway, ASO directed against HER-2 was also able to affect the RR level of ras transformed T24 cells. These findings may be explained in part by the established interaction between the EGF receptor and adaptor protein/guanine nucleotide exchange factor (Grb2/Sos). Buday and Downward have shown that EGF-induced activation of nucleotide exchange on $p21^{ras}$ proceeds through recruitment of Sos to a complex with the EGF receptor and Grb2 at the plasma membrane and that inhibition of this Grb2-EGFR interaction can inhibit activation of ras [Buday, L. and Downward, J. (1993) Cell 73: 611–620]. Therefore, it is conceivable that inhibition of the HER-2 protein by ASO can disrupt this interaction, and thus p21ras nucleotide exchange, and interfere with signalling through ras resulting in decreased RR.

Further support for the existence of the pathway leading to RR is found in the work of Morrison, et al. [1988, PNAS USA 85:8855–8859] and Haimovitz-Friedman, et al. (1991, Can. Res. 51: 2552–2558). These investigators found that bFGF, synthesis of which is stimulated in epithelial cells by γ-irradiation [Haimovitz-Friedman et al. (1991), supra] and which in turn activates Raf-1 protein kinase [Buday and Downward (1993), supra], can protect against radiation-induced cell killing [Haimovitz-Friedman et al. (1991), supra]. Our hypothesis of a signal transduction pathway is further confirmed in a recent report by Kasid et al. which showed that Raf-1 is phosphorylated/activated after exposure to ionizing radiation by upstream protein tyrosine kinases [Kasid, U. et al. (1996) Nature 382: 813–816].

These studies, supporting a pathway, with raf-1 as a central element, leading to cellular radioresistance are also clinically significant in a number of ways. Radiation is one of the major forms of adjuvant therapy for various types of cancer. Understanding the molecular mechanisms leading to the failure of a significant fraction of tumors to respond to radiotherapy opens the door to the development of new methods of intervention to radio-sensitize tumors, resulting in more effective cancer treatments. In this vein, our use of antisense oligonucleotides to radiosensitize human tumor cells not only establishes the signal transduction pathway, but also demonstrates the potential of these molecules as cancer therapeutic agents showing that ASO directed against a focal point in the pathway can be effective in a number of different tumor types. In a similar way, using mouse m5S cells, Taki et al. [Taki, T. et al. (1996) *Bio. Biop. R.* 223:834–438] also recently found that ASO against RAD51, a gene involved in recombination and DNA repair, could increase radiosensitivity.

The use of liposome facilitated delivery of the ASO permits significantly lower effective concentrations of oligomers to be used, a step towards eliminating one of the major drawbacks to the clinical use of antisense therapy. The efficacy of ASO is also advantageous for clinical use. At the concentrations employed in these studies, none of the ASOs increased the sensitivity of control radiosensitive cell lines SCC61 and MCF10A, thereby demonstrating that the use of ASO to ameliorate radioresistance is not deleterious to normal tissues thereby strengthening the potential usefulness of ASO in cancer treatment.

What is claimed is:

1. A method for reducing radiation or drug resistance of a cell, in vitro, which does not overexpress HER-2, said method comprising introducing into said cell an antisense nucleic acid comprising a segment complementary to HER-2 in an amount effective to reduce said radiation or drug resistance.

2. The method of claim 1 wherein said cell is a carcinoma cell selected from the group consisting of breast, bladder, prostate, head, neck, lung, colon, pancreas, cervical, ovarian, and stomach carcinoma cells.

3. The method of claim 1 wherein said antisense nucleic acid is introduced by association with a liposome.

4. The method of claim 1 wherein said antisense nucleic acid comprises SEQ ID NO:3.

5. A method for reducing radiation or drug resistance of a cell, in vitro, which does not overexpress raf-1, said method comprising introducing into said cell an antisense nucleic acid comprising a segment complementary to raf-1 in an amount effective to reduce said radiation or drug resistance.

6. The method of claim 5 wherein said cell is a carcinoma cell selected from the group consisting of breast, bladder, prostate, head, neck, lung, colon, pancreas, cervical, ovarian, and stomach carcinoma cells.

7. The method of claim 5 wherein said antisense nucleic acid is introduced by association with a liposome.

8. The method of claim 5 wherein said antisense nucleic acid comprises SEQ ID NO:1.

9. A method for reducing radiation or drug resistance of a cell, in vitro, which does not comprise a mutant Ha-ras, said method comprising introducing into said cell an antisense nucleic acid comprising a segment complementary to Ha-ras in an amount effective to reduce said radiation or drug resistance.

10. The method of claim 9 wherein said cell is a carcinoma cell selected from the group consisting of breast, bladder, prostate, head, neck, lung, colon, pancreas, cervical, ovarian, and stomach carcinoma cells.

11. The method of claim 9 wherein said antisense nucleic acid is introduced by association with a liposome.

12. The method of claim 9 wherein said antisense nucleic acid comprises SEQ ID NO:2.

* * * * *